(12) United States Patent
Bonsignore et al.

(10) Patent No.: US 7,514,386 B2
(45) Date of Patent: Apr. 7, 2009

(54) CHLORINATED PROMOTERS FOR VANADIUM-BASED POLYMERIZATION CATALYSTS

(75) Inventors: Stefanio Bonsignore, Novara (IT); Marco Ricci, Novara (IT); Antonio Alfonso Proto, Novara (IT); Roberto Santi, Novara (IT); Maria Rivellini, legal representative, Novara (IT); Laura Santi, legal representative, Novara (IT); Stefano Santi, legal representative, Novara (IT); Gian Paolo Ravanetti, Ostiglia (IT); Andrea Vallieri, Bologna (IT)

(73) Assignee: Polimeri Europa S.p.A., Brindisi (IT)

( * ) Notice: Subject to any disclaimer, the term of this patent is extended or adjusted under 35 U.S.C. 154(b) by 514 days.

(21) Appl. No.: 11/137,571

(22) Filed: May 26, 2005

(65) Prior Publication Data

US 2005/0274928 A1 Dec. 15, 2005

(30) Foreign Application Priority Data

May 27, 2004 (IT) .......................... MI2004A1070

(51) Int. Cl.
B01J 31/02 (2006.01)
B01J 31/36 (2006.01)
B01J 27/10 (2006.01)

(52) U.S. Cl. .................. 502/127; 502/118; 502/128; 526/154; 526/159; 526/164; 526/169.2; 526/172; 526/348; 526/339

(58) Field of Classification Search ................ 502/128, 502/127, 118; 526/169.2
See application file for complete search history.

(56) References Cited

U.S. PATENT DOCUMENTS 5,527,951 A * 6/1996 Khan et al. ................. 560/219
5,786,504 A * 7/1998 Nudenberg et al. ......... 560/219
6,228,960 B1 * 5/2001 Tanaglia .................. 526/169.2

OTHER PUBLICATIONS

Brady, W.T. et al. "Some Nucleophilic Addition Reactions of Halogenated 2-Oxetanones" J. Heterocyclic Chem., 1973, vol. 10, 239.*

* cited by examiner

Primary Examiner—Mark Eashoo
Assistant Examiner—Peter F Godenschwager
(74) Attorney, Agent, or Firm—Oblon, Spivak, McClelland, Maier & Neustadt, P.C.

(57) ABSTRACT

Promoters are described for vanadium-based catalysts used in the (co)polymerization of olefins and, in particular, in the production of ethylene/propylene (EPR) or ethylene/propylene/diene (EPDM) elastomeric copolymers. The promoters of the present invention belong to the group of compounds having general formula I:

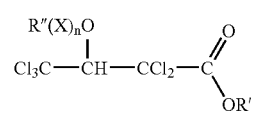

wherein:
"X" represents a (—CO—) carbonyl or (—SO$_2$—) sulfonyl group;
"n" is 0 or 1;
R' is an alkyl or alkylaryl group having from 1 to 20 carbon atoms;
R"=R', H.

15 Claims, No Drawings

CHLORINATED PROMOTERS FOR VANADIUM-BASED POLYMERIZATION CATALYSTS

The present invention relates to chlorinated promoters for vanadium-based catalysts useful in the (co)polymerization of olefins and, in particular, in the production of ethylene/propylene (EPR) or ethylene/propylene/diene (EPDM) elastomeric copolymers.

The use of vanadium-based catalytic systems (in an oxidation state ranging from +3 to +5) and aluminum alkyls (mostly chlorinated) for the polymerization of olefins, has been known for some time. These catalytic systems have been successfully adopted, for example, in the synthesis of ethylene/propylene elastomeric copolymers (G. Natta, G. Mazzanti, A. Valvassori, G. Pajaro, *La Chimica e l'Industria* 1957, 39, 733; G. Natta, G. Mazzanti, A. Valvassori, G. Sartori, D. Fiumani, *J. Polym. Sci.* 1961, 51, 411), of syndiotactic polypropylene (G. Natta, I. Pasquon, A. Zambelli, *J. Am. Chem. Soc.* 1962, 84, 1488) and of ethylene/propylene/diene terpolymers, also elastomeric (D. L. Christman, G. I. Kein, *Macromolecules* 1968, 1, 358).

The activity of these catalytic systems, rapidly decreases with time due to the reduction of the vanadium to species in oxidation state +2, which are catalytically inactive (G. Natta, A. Zambelli, G. Lanzi, I. Pasquon, E. R. Mognaschi, A. L. Segre, P. Centola, *Makromol. Chem.* 1965, 81, 161; E. Addison, A. Deffieux, M. Fontanille, *J. Polym. Sci., Part A: Polymer Chemistry* 1993, 31, 831). In order to increase the polymer yields to acceptable levels for industrial productions, resort is commonly made to a third component of the catalytic system: a promoter capable of reoxidizing the vanadium to catalytically active oxidation states. Polychlorinated organic derivatives are typically used as promoters, normally esters of trichloro-acetic acid (see U.S. Pat. No. 3,301,834). Even more active promoters consist of esters of perchlorobutenoic acids (U.S. Pat. No. 3,622,548; E. Addison, A. Deffieux, M. Fontanille, K. Bujadoux, *J. Polym. Sci., Part A: Polymer Chemistry* 1994, 32, 1033). With respect to the esters of perchlorobutenoic acids, it should be pointed out that, they were initially used without it being possible to decide whether they were derivates of perchlorocrotonic acid or its isomer, perchlorovinylacetic acid. Only more recently it has been possible to establish that they were perchlorovinylacetic derivatives but they can still frequently be found in scientific and patent literature as esters of perchlorocrotonic acid. At present, however, the use of these derivatives of perchlorovinylacetic acid has been discouraged due to the fact that the raw material used in their preparation (A. Rodeig, P. Bernemann, *Liebigs Ann. Chem.* 1956, 1, 600) is hexachlorobutadiene, a carcinogenic product.

A first object of the present invention relates to chlorinated promoters for vanadium-based catalysts useful in the (co) polymerization of olefins and, in particular, in the production of ethylene/propylene (EPR) or ethylene/propylene/diene (EPDM) elastomeric copolymers.

The chlorinated promoters of the present invention are at least just as efficient as the esters of perchlorobutenoic acids but, at the same time, they can be prepared from raw materials which are less dangerous than hexachlorobutadiene and, in any case, are not carcinogenic.

A second object of the present invention relates to a new method for the preparation of the above chlorinated promoters.

The chlorinated promoters of the present invention are characterized by general formula I:

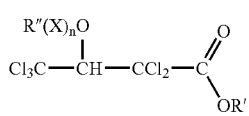

wherein:
- X represents a (—CO—) carbonyl or (—SO$_2$—) sulfonyl group;
- n is 0 or 1;
- R' is an alkyl or alkylaryl group having from 1 to 20 carbon atoms;
- R" =R', H.

Of these compounds, 2,2,4,4,4-pentachloro-3-hydroxybutanoic acid (1; n=0, R'=R"=H) and its methyl ester (1; n=0, R'=CH$_3$, R"=H) are already known, both prepared by the reaction (with water or methanol, respectively) of 3,3-dichloro-4-trichloromethyl-2-oxethanone, in turn obtained in situ by reaction (cyclo-addition) between dichloroketene and chloral (W. T. Brady, A. D. Patel, *J. Heterocyclic Chem.* 1973, 10, 239):

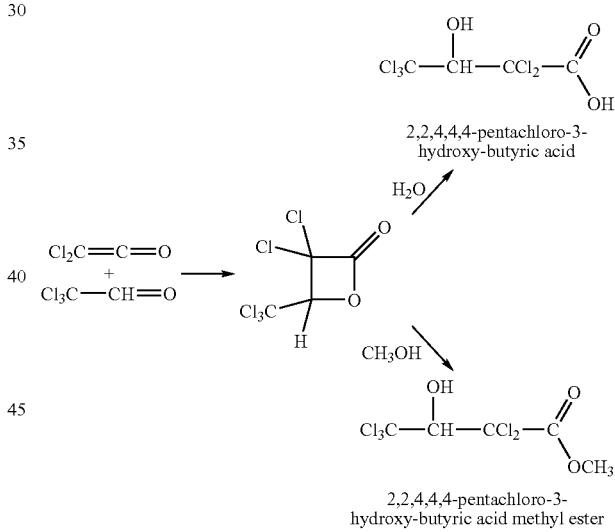

It has now been found that the esters of 2,2,4,4,4-pentachloro-3-hydroxybutyric acid (1; n=0, R"=H) can be more conveniently prepared by means of a Reformatsky reaction between the corresponding esters of trichloroacetic acid and trichloroacetaldehyde with the formation of esters of 2,2,4,4,4-pentachloro-3-hydroxybutyric acid which are included in general formula 1 (with n=0, R"=H):

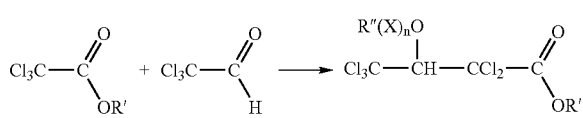

These esters can be used as such or, alternatively, the hydroxyl group can be functionalized with suitable reagents so as to obtain products having general formula 1 wherein n=1:

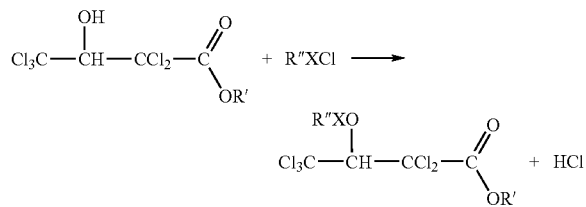

In accordance with this, the present invention relates to a process for the preparation of the compounds having general formula (1)

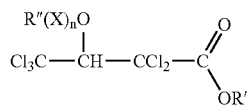

wherein:
X represents a (—CO—) carbonyl or (—SO$_2$—) sulfonyl group;
n is 0 or 1;
R' is an alkyl or alkylaryl group having from 1 to 20 carbon atoms, optionally halogen substituted;
R"=R', H.

which comprises:
(i) a first step for the preparation of the compounds having general formula (Ia) wherein n=0, R"=H, R' having the meaning defined above, obtained by reacting, in the presence of zinc, trichloro-acetaldehyde and esters of trichloroacetic acid;
(ii) an optional second step in which the compound having general formula (Ia) obtained at the end of step (i) is transformed according to the conventional techniques into the compound having general formula (I) wherein:
(a) n=1, X is selected from —CO— and —SO$_2$—, R"=alkyl or alkylaryl; or
(b) n=0, R"=alkyl or alkylaryl.

The Reformatsky reaction (i.e. step I) is carried out with zinc powder starting from esters of trichloroacetic acid Cl$_3$CCOOR' (wherein R' has the meaning defined above) and anhydrous trichloroacetaldehyde. The reaction is effected at temperatures ranging from −15° C. to +70° C., in an inert atmosphere (generally under nitrogen) and in anhydrous solvents, such as tetrahydrofuran (THF), 1,2-dimethoxyehtane, ethyl ether, benzene, toluene, etc. The best solvent is THF. The trichloroacetic ester/zinc molar ratio is lower than 1, preferably from 0.5 to 1. The trichloroacetic ester/trichloroacetaldehyde molar ratio is, on the other hand, higher than 1, preferably from 1 to 2. The quantity of solvent is not critical: final concentrations of trichloroacetic ester ranging from 0.5 to 1.5 M ensure satisfactory results. The duration of the reaction depends on the conditions adopted and, in particular, on the temperature and concentrations of the reagents: reaction times ranging from 1 to 5 hours are normally sufficient.

It is convenient to activate the zinc powder before the reaction: said activation is suitably obtained by washing the powder for 1-10 minutes with hydrochloric acid at 5%, filtering it and washing it, in order, with water, acetone and petroleum ether. It is finally dried for a few hours at 110° C. at reduced pressure. Alternative methods and procedures can also be used, however, for example, activation with ultrasounds.

The esters of 2,2,4,4,4-pentachloro-3-hydroxybutyric acid obtained from the Reforatsky reaction at the end of step (i) can be functionalized with suitable reagents and according to the known techniques, so as to transform the hydroxyl into esters or sulfonates (n=1, X=—CO— or —SO$_2$—), or into ethers (n=0, R" selected from alkyl and alkylaryl).

In particular, the compounds obtained at the end of step (i) can be reacted with acyl chlorides (obtaining the products having general formula 1 wherein n=1 and X=—CO—) or sulfonic acid chlorides (obtaining the products having general formula 1 wherein n=1 and X=—SO$_2$—). In both cases, the reaction is carried out in the presence of a base. (for example, triethylamine), in solvents such as THF or methylene chloride. The duration of this reaction depends on the conditions adopted and, in particular, on the temperature (generally at room temperature and atmospheric pressure) and on the concentrations of the reagents and base (which are not critical and can vary within wide ranges): times ranging from 0.5 hours to 5 hours are generally sufficient for carrying out the reaction.

Acyl chlorides which can be conveniently used are, for example, chlorides of acetic, propionic, butanoic (or butyric), pentanoic (or valerianic), hexanoic (or capronic), heptanoic (or enanthic), octanoic (or caprylic), 2-ethylhexanoic, nonanoic (or pelargonic), decanoic (or caprinic), dodecanoic (or lauric), tetradecanoic (or myristic), hexadecanoic (or palmitic), octadecanoic (or stearic) acids, etc.

Sulfonic acid chlorides which can be conveniently used are, for example, those of methanesulfonic, trifluoromethanesulfonic, trichloromethanesulfonic, benzenesulfonic, p-toluenesulfonic acids, etc.

The molar ratio between the acid chloride and base is not critical but it is convenient to use a ratio at least equal to 1 and ranging, for example, from 1 to 2. The molar ratio between the ester of 2,2,4,4,4-pentachloro-3-hydroxybutyric acid and the acid chloride is lower than or equal to 1 and preferably ranges from 0.4 to 1.

Alternatively, the compound having general formula (Ia) can be transformed into ether. These reaction conditions are typically the same as those used by experts in the field for transforming an —OH— into an OR" ether.

A second aspect of the present invention relates to a process for the (co)polymerization of olefins, in particular, for the preparation of ethylene/propylene (EPR) or ethylene/propylene/diene (EPDM) elastomeric copolymers, the above process being carried out in the presence of a catalytic system comprising:
(a) a vanadium complex having the general formula $L_pVO_q$ wherein: i) p is an integer ranging from 2 to 4; ii) q can have the values of 0 or 1; iii) the sum p+q must be 3 or 4; and iv) L is a halogen, preferably Cl, or a beta-dicarbonyl group such as acetylacetonate, formylacetonate, benzoylacetonate and, preferably, acetylacetonate.
(b) a chlorinated aluminum alkyl having the general formula $Al_yR'''_{3y-z}Cl_z$, wherein: R''' represents a linear or branched alkyl group, containing from 1 to 20, preferably from 1 to 4, carbon atoms; "y"=1 or 2; "z" is an integer ranging from 1 to 3y−1;
(c) a chlorinated promoter selected from one or more compounds having general formula 1.

Typical examples of chlorinated aluminum alkyls which can be advantageously used are: AlEt$_2$Cl (diethylchloroaluminum), AlMe₂Cl (dimethylaluminumchloride), AlEtCl₂ (ethylaluminumdichloride), Al(i-Bu)₂Cl (diisobutylaluminum chloride), Al₂Et₃Cl₃ (ethylaluminumsesquichloride), Al₂Me₃Cl₃ (methylaluminumsesquichloride). In the preferred embodiment the chlorinated aluminum alkyls used are AlEt₂Cl (diethyl-chloro-aluminum) or Al₂Et₃Cl₃ (ethylaluminumsesquichloride).

The molar ratio between the chlorinated aluminum alkyl and the vanadium complex ranges from 1 to 1,000, preferably from 3 to 100, even more preferably from 5 to 50.

The molar ratio between the chlorinated promoter having general formula 1 and the vanadium ranges from 1 to 40, preferably from 1 to 10.

The catalytic systems thus defined are used in (co)polymerization processes of α-olefins in liquid phase (solution or suspension) at low or medium pressure (5-50 atm) and at temperatures ranging from −5 to 75° C. In the preferred embodiment, the temperature ranges from 10 to 30° C. and the pressure from 5 to 20 atm.

The polymers and copolymers obtained generally have very high average molecular weights but, if lower molecular weights are desired, it is possible to use hydrogen as molecular weight regulator.

The catalyst for the (co)polymerization of α-olefins is prepared by contact of the vanadium complex, dissolved in an aliphatic or aromatic hydrocarbon solvent, with the chlorinated aluminum alkyl and with the promoter having general formula 1. The contact can take place:

- separately (in the absence of the mixture of olefins to be polymerized), for a time ranging from 1 to 30 minutes (and preferably from 5 to 20 minutes), at a temperature ranging from 0 to 50° C. (and preferably from 15 to 40° C.), or
- in the polymerization reactor, in the presence of the mixture of monomers. In this case, the three reagents can be added separately or as a mixture of two of these. The catalyst is preferably formed in situ by introducing the chlorinated aluminum alkyl into the autoclave already containing the solvent or suspending agent (heptane or liquid propylene), the reagent mixture and, optionally, the termonomer, and adding the solution in toluene or mesitylene of the vanadium complex and of the promoter having general formula 1.

The catalysts described can be used in the polymerization of α-olefins and, in particular, preferably in the polymerization of ethylene, in the copolymerization of ethylene with propylene and higher α-olefins and in the terpolymerization of ethylene with propylene and dienes to give polymers having densities ranging from 0.86 g/cm³ to 0.96 g/cm³.

The copolymerization of ethylene and propylene to give EPR elastomeric copolymers and the terpolymerization of ethylene, propylene and a non-conjugated diene to give EPDM rubbers, are of particular interest. In this latter case, the diene can be selected from: i) linear chain aliphatic dienes such as 1,4-hexadiene and 1,6-octadiene; ii) branched chain acyclic dienes such as 5-methyl-1,4-hexadiene, 3,7-dimethyl-1,6-octadiene, 3,7-dimethyl-1,7-octadiene; iii) single chain alicyclic dienes such as 1,4-cyclohexadiene, 1,5-cyclooctadiene; iv) dienes having condensed and bridged alicyclic rings such as methyltetrahydroindene, 5-ethylidene-2-norbornene (ENB), 5-propenyl-2-norbornene.

In the preferred embodiment, the diene is ENB or 1-methylene-2-vinyl-cyclopentane.

The EPR and EPDM elastomeric copolymers that can be obtained with the catalysts described contain from 20 to 65% in moles of propylene and quantities not higher than 15% of ENB. The weight average molecular weight of the polymer obtained in the presence of hydrogen varies from 50,000 to 700,000.

The following examples are provided for a better understanding of the present invention.

EXAMPLES

Molecular Weight Determination

The molecular weights are determined by means of Gel Permeation Chromatography, (GPC) in 1,2,4-trichlorobenzene (stabilized with N,N'-m-phenylenedimaleimide) at 135° C. with a 150-CV Waters chromatograph, using a differential refractometer (Waters) as detector. The chromatographic separation was obtained with a set of HT μ Styragel columns (Waters) with pore dimensions of $10^3$, $10^4$, $10^5$ and $10^6$ Å, establishing a flow-rate of the effluent of 1 ml/min. The data were acquired and processed by means of Maxima 820 software version 3.30 (Millipore). The calibration curve used for the calculation of the number average molecular weights ($M_n$) and weight average molecular weights ($M_w$) was obtained using standard polystyrene samples with molecular weights within the range of 2,000-6,500,000 and applying the Mark-Houwink equation valid for linear polyethylene and polypropylene; the values were then corrected in relation to the composition of the polymer using the Scholte equation.

Propylene Content

The propylene content in the ethylene-propylene copolymers is determined on samples in the form of film using an FTIR Perkin-Elmer 1,800 spectrometer with a resolution of 4 $cm^{-1}$ and 64 scannings, by measuring the band absorptions at 4390 and 4255 $cm^{-1}$, (4390, 4330, 4255 and 1688 $cm^{-1}$ in the ethylene-propylene-ENB terpolymers) and on the basis of calibration curves set up with copolymers (terpolymers) having a known composition.

Example 1

Synthesis of ethyl 2,2,4,4,4-pentachloro-3-hydroxybutyrate (Formula I: R'=C₂H₅; n=0; R''=H)

1a) Zinc Activation 50 g of zinc in powder form are suspended in 600 ml of a solution of hydrochloric acid at 5%. The mixture is stirred vigorously for about five minutes, the zinc is filtered, washed with water until neutrality of the washing water and then again with acetone, and finally with petroleum ether. It is dried at reduced pressure ($2\times10^{-3}$ mbar) at 110° C. for 4 hours.

1b) Synthesis of ethyl 2,2,4,4,4-pentachloro-3-hydroxy-butyrate in THF at −10° C.

39.23 g of activated zinc powder (0.6 moles) in 200 ml of anhydrous tetrahydrofuran are suspended in an inert atmosphere, and about 10 ml of a solution consisting of 114.86 g of ethyl trichloro-acetate (0.6 moles) in 100 ml of anhydrous tetrahydrofuran are added. The whole mixture is heated under reflux conditions (about 70° C.) in order to activate the reaction and is then cooled to −10° C. What remains of the solution of ethyl trichloro-acetate in tetrahydrofuran is added dropwise for about one hour and then stirred for a further 4 hours. A solution of 73.65 g of anhydrous trichloro acetaldehyde (0.5 moles) in 100 ml of anhydrous tetrahydrofuran is then added dropwise, over a period of 1 hour, the temperature is left to rise to 20° C. and the whole mixture is stirred for a further hour. The reaction mass is poured into 400 ml of a 5% solution of hydrochloric acid, it is extracted with ethyl acetate (or ethyl ether), washed to neutrality with a sodium chloride saturated solution, anhydrified with anhydrous sodium sulphate and evaporated at reduced pressure to remove the solvent and about 7% of non-reacted ethyl trichloro-acetate. 136.0 g of product are obtained having a gas-chromatographic purity of 94% (yields: 84% with respect to trichloro-acetaldehyde; 70% with respect to ethyl trichloro-acetate).

Example 2

Synthesis of ethyl 2,2,4,4,4-pentachloro-3-hydroxy butyrate in THF at 0° C.

7.0 g of activated zinc powder (0.11 moles) in 80 ml of anhydrous tetrahydrofuran are suspended in an inert atmosphere, and about 2 ml of a solution consisting of 19.14 g of ethyl trichloro-acetate (0.1 moles) in 20 ml of anhydrous tetrahydrofuran are added. The whole mixture is heated under reflux conditions (about 70° C.) in order to activate the reaction and is then cooled to 0C. What remains of the solution of ethyl trichloro-acetate in tetrahydrofuran is added dropwise over a period of about one hour and then stirred for a further 3 hours. A solution of 11.8 g of anhydrous trichloro-acetaldehyde (0.08 moles) in 20 ml of anhydrous tetrahydrofuran is then added dropwise, over a period of an hour, the temperature is left to rise to 20° C. and the mixture is stirred for a further hour. The reaction mass is poured into 150 ml of a 5% solution of hydrochloric acid, it is extracted with ethyl acetate (or ethyl ether), washed to neutrality with a sodium chloride saturated solution, anhydrified with anhydrous sodium sulphate and evaporated at reduced pressure to remove the solvent and about 10% of non-reacted ethyl trichloro-acetate. 21.5 g of product are obtained having a gas-chromatographic purity of 95% (yields: 84% with respect to trichloro acetaldehyde; 67% with respect to ethyl trichloro-acetate).

Example 3

Synthesis of ethyl 2,2,4,4,4-pentachloro-3-hydroxy butyrate in THF at 15° C.

3.6 g of activated zinc powder (0.055 moles) in 20 ml of anhydrous tetrahydrofuran are suspended in an inert atmosphere, and about 1 ml of a solution consisting of 9.57 g of ethyl trichloro-acetate (0.05 moles) in 8 ml of anhydrous tetrahydrofuran is added. The whole mixture is heated under reflux conditions (about 70° C.) in order to activate the reaction and is then cooled to 15° C. What remains of the solution of ethyl trichloro-acetate in tetrahydrofuran is added dropwise over a period of about one hour, the dripping being regulated so as to keep the temperature constant. At the end, the stirring is continued for a further hour. A solution of 5.9 g of anhydrous trichloroacetaldehyde (0.04 moles) in 4 ml of anhydrous tetrahydrofuran is then added dropwise, over a period of 30 minutes, the temperature is left to rise to room temperature and the mixture is stirred for a further hour. The reaction mass is poured into 100 ml of a 5% solution of hydrochloric acid, it is extracted with ethyl acetate (or ethyl ether), washed to neutrality with a sodium chloride saturated solution, anhydrified with anhydrous sodium sulphate and evaporated at reduced pressure to remove the solvent and about 10% of non-reacted ethyl trichloro-acetate. 10.9 g of product are obtained having a gas-chromatographic purity of 96% (yields: 86% with respect to trichloro acetaldehyde; 69% with respect to ethyl trichloro-acetate).

Example 4

Synthesis of ethyl 2,2,4,4,4-pentachloro-3-hydroxy butyrate in THF at 15° C. with a Higher Zinc Excess The same procedure is adopted as in example 3, but using 4.0 g of activate zinc powder (0.06 moles) and 6.26 g of anhydrous trichloro-acetaldehyde (0.0425 moles). At the end of the reaction, no non-reacted ethyl trichloro-acetate remains.

11.6 g of product are obtained having a gas-chromatographic purity of 94% (yields: 84% with respect to trichloro-acetaldehyde; 71% with respect to ethyl trichloro-acetate).

Example 5

Synthesis of ethyl 2,2,4,4,4-pentachloro-3-hydroxy butyrate in 1,2-dimethoxy ethane at −15° C.

7.00 g of activated zinc powder (0.11 moles) in 80 ml of anhydrous 1,2-dimethoxy ethane are suspended in an inert atmosphere, and about 2 ml of a solution consisting of 19.14 g of ethyl trichloro-acetate (0.1 moles) in 20 ml of anhydrous 1,2-dimethoxy ethane are added. The whole mixture is heated to about 70° C. in order to activate the reaction and is then cooled to −15° C. What remains of the solution of ethyl trichloro-acetate in 1,2-dimethoxy ethane is added dropwise over a period of about one hour. The temperature is left to rise to 15° C. and then stirred for a further two hours. The reaction mass is cooled again to −15° C. and a solution of 11.8 g of anhydrous trichloro-acetaldehyde (0.08 moles) in 20 ml of anhydrous 1,2-dimethoxy ethane is then added dropwise, over a period of about one hour, the temperature is subsequently left to rise to 20° C. and the mixture is stirred for a further hour. The reaction mass is poured into 200 ml of a 5% solution of hydrochloric acid, it is extracted with ethyl acetate (or ethyl ether), washed to neutrality with a sodium chloride saturated solution, anhydrified with anhydrous sodium sulphate and evaporated at reduced pressure to remove the solvent and about 10% of non-reacted ethyl trichloro-acetate. 20.7 g of product are obtained having a gas-chromatographic purity of 93% (yields: 79% on trichloro-acetaldehyde; 63% on ethyl trichloro-acetate).

Example 6

Synthesis of ethyl 2,2,4,4,4-pentachloro-3-acetoxybutyrate (Formula 1: R'=$C_2H_5$; n=1; x=CO; R"=$CH_3$)

A solution is prepared, operating at room temperature, of 1.4 g (4.6 mmoles) of ethyl 2,2,4,4,4-pentachloro-3-hydroxybutyrate and 0.51 g (5 mmoles) of triethylamine in 20 ml of anhydrous tetrahydrofuran and a second solution of 0.39 g (5 mmoles) of acetylene chloride in 10 ml of anhydrous tetrahydrofuran is dripped into the first solution.

At the end of the dripping, the reaction mass is stirred for a further 30 minutes, it is then poured into 100 ml of water, extracted with ethyl acetate (or ethyl ether), washed with a saturated solution of sodium chloride until neutrality of the washing water, anhydrified with anhydrous sodium sulphate and the solvent is evaporated under reduced pressure. 1.45 g of ethyl 2,2,4,4,4-pentachloro-3-acetoxybutyrate are obtained, having a gas-chromatographic purity of 96% (yield with respect to ethyl 2,2,4,4,4-pentachloro-3-hydroxybutyrate: 87%).

Example 7

Synthesis of ethyl 2,2,4,4,4-pentachloro-3-heptanoyl-butyrate [Formula 1: R'=$C_2H_5$; n=1; x=CO; R"=$CH_3(CH_2)_5$]

A solution is prepared, operating at room temperature, of 1.85 g (6.08 mmoles) of ethyl 2,2,4,4,4-pentachloro-3-hydroxybutyrate and 0.54 g (6.3 mmoles) of triethylamine in 20 ml of anhydrous tetrahydrofuran, and a second solution of 0.94 g (6.3 mmoles) of heptanoyl chloride in 10 ml of anhydrous tetrahydrofuran is dripped into the first solution.

At the end of the dripping, the reaction mass is stirred for a further 30 minutes, it is then poured into 100 ml of water, extracted with ethyl acetate (or ethyl ether), washed with a saturated solution of sodium chloride until neutrality of the washing water, anhydrified on anhydrous sodium sulphate and the solvent is evaporated under reduced pressure. 2.14 g of ethyl 2,2,4,4,4-pentachloro-3-heptanoylbutyrate are obtained having a gas-chromatographic purity of 90% (yield with respect to ethyl 2,2,4,4,4-pentachloro-3-hydroxybutyrate: 76%).

Example 8

Synthesis of ethyl 2,2,4,4,4-pentachloro-3-trifluoromethanesulfonyloxybutyrate (Formula 1: R'=$C_2H_5$; n=1; x=$SO_2$; R"=$CF_3$)

A solution is prepared, operating at room temperature, of 1.0 g (3.29 mmoles) of ethyl 2,2,4,4,4-pentachloro-3-hydroxybutyrate and 0.4 g (4 mmoles) of triethylamine in 15 ml of anhydrous methylene chloride, and a second solution of 1.18 g (7 mmoles) of trifluoromethanesulfonylchloride in 5 ml of anhydrous methylene chloride is dripped into the first solution.

At the end of the dripping, the reaction mass is stirred for a further 4 hours, it is then poured into 50 ml of water, extracted with ethyl acetate (or ethyl ether), washed with a saturated solution of sodium chloride until neutrality of the washing water, anhydrified on anhydrous sodium sulphate and the solvent is evaporated under reduced pressure. 0.80 g of residue are obtained, which are purified on a silica column (eluant: hexane/ethyl acetate 80/20). 0.34 g of ethyl 2,2,4,4,4-pentachloro-3-trifluoromethansulfonyloxybutyrate are recovered from the column, having a gas-chromatographic purity of 98% (yield with respect to ethyl 2,2,4,4,4-pentachloro-3-hydroxy butyrate: 23%).

Example 9

Ethylene-propylene Co-Polymerization in Solution in the Presence of ethyl 2,2,4,4,4-pentachloro-3-hydroxybutyrate (Formula 1: R'=$C_2H_5$; n=0; R"=H) as Promoter Nitrogen-vacuum is effected, for at least three times at a temperature of 90° C. and for an overall period of about 2 hours, in a 2 l steel autoclave, equipped with a burette for the addition of the catalyst, a helix stirrer, thermo-resistance and a heating jacket connected to a thermostat for the temperature control. A flushing of the reactor is effected before each test, by maintaining under stirring, at 90° C., a solution containing 500 ml of anhydrous heptane and 5 ml of Al(i-Bu)$_3$ for about two hours. The contents of the reactor are discharged through a valve situated at the bottom, under a slight nitrogen pressure and a solution is poured into the autoclave, containing 1 l of heptane and 0.26 ml of diethyl aluminum chloride (2.1 mmoles). The autoclave is pressurized introducing in order: 200 g of propylene (4.9 atm) and 7 g of ethylene (1 atm) and the mixture is thermostat regulated at 30° C. At this point, a solution is introduced, through the burette situated at the head of the autoclave, by means of a slight nitrogen over-pressure, containing 0.042 mmoles of V(acac)$_3$ (aluminum/vanadium molar ratio: 50) and, as promoter, 0.25 mmoles of ethyl 2,2,4,4,4-pentachloro-3-hydroxybutyrate in 10 ml of toluene (promoter/vanadium molar ratio: 6). Once the catalyst has been introduced, the system is maintained for 20 minutes at a constant pressure by means of an ethylene flow. At the end, the contents of the reactor are discharged under pressure by means of the bottom valve and coagulated in about 3 l of ethanol. The polymer is separated by filtration, washed with acetone and anhydrified under vacuum at 40° C. for about 8 hours.

41.1 g of an ethylene-propylene copolymer are obtained having a propylene content of 34.7% in moles, a $M_w$ value of 234,000 and a molecular weight distribution of 2.5.

Example 10

Copolymerization of ethylene-propylene in Solution in the Presence of ethyl 2,2,4,4,4-pentachloro-3-trifluoromethansulfonyloxybutyrate (Formula 1: R'=$C_2H_5$; n=1; x=$SO_2$; R"=$CF_3$) as Promoter The same procedure is adopted as in example 9, with the only variation that ethyl 2,2,4,4,4-pentachloro-3-trifluoromethansulfonyloxybutyrate is used as promoter.

47.9 g of an ethylene-propylene copolymer are obtained, having a propylene content of 38.6% in moles, an $M_w$ value of 190,000 and a molecular weight distribution of 2.6.

Example 11

Copolymerization of ethylene-propylene in Solution in the Presence of ethyl 2,2,4,4,4-pentachloro-3-acetoxybutyrate (Formula 1: R'=$C_2H_5$; n=1; x=CO; R"=$CH_3$) as Promoter The same procedure is adopted as in example 9, with the only variation that ethyl 2,2,4,4,4-pentachloro-3-acetoxybutyrate is used as promoter.

44.6 g of an ethylene-propylene copolymer are obtained, having a propylene content of 37.9% in moles, an $M_w$ value of 171,000 and a molecular weight distribution of 2.4.

Example 12

Copolymerization of ethylene-propylene in Solution in the Presence of ethyl 2,2,4,4,4-pentachloro-3-heptanoyloxy-butyrate [Formula 1: R'=$C_2H_5$; n=1; x=CO; R"=$CH_3(CH_2)_6$] as Promoter The same procedure is adopted as in example 9, with the only variation that ethyl 2,2,4,4,4-pentachloro-3-heptanoyloxybutyrate is used as promoter.

43.4 g of an ethylene-propylene copolymer are obtained, having a propylene content of 36.6% in moles, an $M_w$ value of 163,000 and a molecular weight distribution of 2.3.

Comparative Example 13

Copolymerization of ethylene-propylene in Solution in the Presence of ethyl trichloro-acetate as Promoter The same procedure is adopted as in example 9, with the only variation that ethyl trichloro-acetate is used as promoter.

29.7 g of an ethylene-propylene copolymer are obtained, having a propylene content of 35.3% in moles, an $M_w$ value of 186,000 and a molecular weight distribution of 2.7.

Example 14

Ethylene-propylene Copolymerization in Suspension in the Presence of ethyl 2,2,4,4,4-pentachloro-3-hydroxybutyrate (Formula 1: $R'=C_2H_5$; n=0; $R''=H$) as Promoter A 3 l steel autoclave is used for the experiment, equipped with a burette for the addition of the catalyst solution, a stirrer at 400 rpm with two axial impellers, a thermostat-regulation system of the jacket and split-range plate exchanger valves (with a cooling cycle at 0° C. and Boyler at 50° C.) and a DCS control system. Before the test, the reactor is flushed by stirring, at 30° C., a solution of 2,000 ml of liquid propylene and 5 ml of DEAC 1 M in n-hexane for 60 minutes. The flushing solution is then discharged and the reactor is washed with 2,000 ml of liquid propylene. The reaction is prepared by introducing, in order: 0.6 bar of $H_2$, 2,000 ml of propylene and 8 mmoles of diethyl aluminum chloride (8 ml of 1 M solution). The reactor is brought to a temperature of 20° C. and is pressurized with 50 g of ethylene, thus obtaining a total pressure of 13 bar. At this point, a solution containing 0.025 mmoles of V(acac)$_3$ (5 ml of 0.00491 M solution in mesitylene; aluminum/vanadium molar ratio=320) and 0.37 mmoles of ethyl 2,2,4,4,4-pentachloro-3-hydroxybutyrate in 20 ml of n-hexane (promoter/vanadium molar ratio=15) as promoter, are introduced (by means of a slight nitrogen overpressure) through the burette situated on the top of the autoclave. Once the catalyst mixture has been introduced, the polymerization starts and the reaction is stopped after 10 minutes, introducing, under a nitrogen over-pressure, 25 ml of a solution of ethyl alcohol with 0.8% of antioxidant Anox PP18 and 0.2% of talc. After drying and calendering, 90 g of ethylene-propylene copolymer are recovered, having a propylene content of 28-29% in moles, a Mooney viscosity at 125° (1+4) of 80-90, an $M_w$ value of 220,000 and a molecular weight distribution of 2.0. The yield is 70.9 kg of polymer per g of vanadium.

Example 15

Ethylene-propylene Copolymerization in Suspension in the Presence of ethyl 2,2,4,4,4-pentachloro-3-acetoxybutyrate (Formula 1: $R'=C_2H_5$; n=1; x=CO; $R''=CH_3$) as Promoter The same procedure is adopted as in example 14, with the only variation that ethyl 2,2,4,4,4-pentachloro-3-acetoxy-butyrate is used as promoter.

After drying and calendaring, 95 g of ethylene-propylene copolymer are recovered, having a propylene content of 28-29% in moles, a Mooney viscosity at 125° (1+4) of 80-90, an $M_w$ value of 220,000 and a molecular weight distribution of 2.0. The yield is 74.8 kg of polymer per g of vanadium.

Example 16

Ethylene-propylene Copolymerization in Suspension in the Presence of ethyl 2,2,4,4,4-pentachloro-3-heptanoyloxy-butyrate [Formula 1: $R'=C_2H_5$; n=1; x=CO; $R''=CH_3(CH_2)_6$] as Promoter (See Table 3)

The same procedure is adopted as in example 14, with the only variation that ethyl 2,2,4,4,4-pentachloro-3-heptanoyloxybutyrate is used as promoter.

After drying and calendaring, 97 g of ethylene-propylene copolymer are recovered, having a propylene content of 28-29% in moles, a Mooney viscosity at 125° (1+4) of 80-90, an $M_w$ value of 220,000 and a molecular weight distribution of 2.0. The yield is 76.4 kg of polymer per g of vanadium.

Example 17

Ethylene-propylene Copolymerization in Suspension, on a Pilot Scale, in the Presence of ethyl 2,2,4,4,4-pentachloro-3-hydroxybutyrate (Formula 1: $R'=C_2H_5$; n=0; $R''=H$) as Promoter (See Table 3)

A pilot plant is used for the experimentation, having a 60 liter CSTR reactor. The feeding of the monomers and components of the catalyst mixture is effected through microdosing pumps which suck the chemicals from tanks and send them onto a feeding comb. DEAC is fed separately. The reaction is carried out with an average volume of 40 liters, with an average residence time of 1 hour (28 liters/hour of propylene and 12 liters/hour of propane). The final composition and conditions of the reaction mixture in gas phase are the following: 0.45% of hydrogen; 9.05% of ethylene; 63.35% of propylene; 27.15% of propane; temperature 20° C.; pressure 10 bar. The polymerization is carried out with level control of the reactor which discharges in continuous onto two 400 liter strippers filled with water, with the addition of 2% of a solution containing soda and talc and heated with vapour to 60° C. After 40 hours of polymerization, 829.5 g of DEAC were fed (6.88 moles) together with 3.00 g of vanadium acetylacetonate (8.6 mmoles; aluminum/vanadium molar ratio=800) and 33.26 g of ethyl 2,2,4,4,4-pentachloro-3-hydroxybutyrate (0.109 moles; promoter/vanadium molar ratio=12.7), and 25 kg of an ethylene-propylene copolymer were obtained with a propylene content of 46-47% in moles, a Mooney viscosity at 125° (1+4) of 60-70, an $M_w$ value of 200,000 and a molecular weight distribution of 2.0. The yield is 57.1 kg of polymer per g of vanadium. Considering that a process simulation shows that, by feeding a CSTR with an average residence time of 1 hour, 30% of the catalyst does not react, the actual yield is 81.5 kg of polymer per g of vanadium.

Example 18

Ethylene-propylene-ENB Terpolymerization in Suspension, on a Pilot Scale, in the Presence of ethyl 2,2,4,4,4-pentachloro-3-hydroxybutyrate (Formula 1: $R'=C_2H_5$; n=0; $R''=H$) as Promoter (See Table 3)

The same pilot plant is used as in Example 17. The reaction is carried out with an average volume of 40 litres with an average residence time of 1 hour (30 litres/hour of propylene and 10 litres/hour of propane).

The final composition and conditions of the reaction mixture in gas phase are as follows: 20.38% of ethylene; 56.53% of propylene; 23.09% of propane; temperature 20° C.; pressure 10 bar. Hydrogen is absent. After 30 hours of polymerization, 541.3 g of DEAC were fed (4.49 moles) together with 1.95 g of vanadium acetylacetonate (5.6 mmoles; aluminum/vanadium molar ratio=802); 20.39 g of ethyl 2,2,4,4,4-pentachloro-3-hydroxybutyrate (0.067 moles; promoter/vanadium molar ratio=12) and 6.5 Kg of ENB, and 20 kg of a terpolymer containing 33-34% of propylene and 7-8% of ENB, were obtained with an $M_w$ value of about 600,000 and a molecular weight distribution of 2.5. The yield is 70.1 kg of polymer per g of vanadium. Considering that a process simulation shows that, by feeding a CSTR with an average residence time of 1 hour, 30% of the catalyst does not react, the actual yield is 100.0 kg of polymer per g of vanadium.

Example 19

Ethylene-propylene Copolymerization in Suspension in the Presence of ethyl trichloro-acetate as Promoter
(See Table 3)

The same procedure is adopted as in Example 14, with the only variation that ethyl trichloro-acetate is used as promoter.

78 g of a copolymer having the same composition and molecular weight distribution are obtained, and therefore with a yield of 61.4 Kg of polymer per g of vanadium, but with an ethylene-propylene reactivity ratio (Re*Rp) of 0.9 against 0.5 of the copolymer obtained in Example 14.

TABLE 1

|  | X | n | R''' | R' |
|---|---|---|---|---|
| Ex. 1 (P1) | — | 0 | H | —C$_2$H$_5$ |
| Ex. 2 (P1) | — | 0 | H | —C$_2$H$_5$ |
| Ex. 3 (P1) | — | 0 | H | —C$_2$H$_5$ |
| Ex. 4 (P1) | — | 0 | H | —C$_2$H$_5$ |
| Ex. 5 (P1) | — | 0 | H | —C$_2$H$_5$ |
| Ex. 6 (P2) | —CO— | 1 | CH$_3$ | —C$_2$H$_5$ |
| Ex. 7 (P3) | —CO— | 1 | CH$_3$(CH$_2$)$_6$— | —C$_2$H$_5$ |
| Ex. 8 (P4) | —SO$_2$— | 1 | CF$_3$ | —C$_2$H$_5$ |

TABLE 2

Ethylene-propylene copolymerization in solution

|  | Activity | Yield (grams) | Bound propylene % Mol. | $M_w$ | $M_w/M_n$ |
|---|---|---|---|---|---|
| Ex. 9 | P1 | 41.1 | 34.7 | 234000 | 2.5 |
| Ex. 10 | P4 | 47.9 | 38.6 | 190000 | 2.6 |
| Ex. 11 | P2 | 44.6 | 37.9 | 171000 | 2.4 |
| Ex. 12 | P3 | 43.4 | 36.6 | 163000 | 2.3 |
| Comp. Ex. 13 | TRCl | 29.7 | 35.3 | 186000 | 2.7 |

Note:
TRCl = ethyl trichloro-acetate

From the data of table 2, it can be easily observed that the use of the claimed activators leads to an increase in the yields of about 50% with respect to the comparative example. The characteristics of the polymer, in terms of incorporation of the comonomer, the molecular weights and relative distributions, remain substantially unvaried.

TABLE 3

Ethylene-propylene copolymerization in suspension

| Ex. | Activity | Yield [kg/g$_v$] | C$_3$ [% mol] | r$_E$xr$_P$ | Mooney | Mw × 1000 | MWD |
|---|---|---|---|---|---|---|---|
| 14 | P1 | 90 | 28-29 | 0.5 | 80-90 | 220 | 2.0 |
| 15 | P2 | 95 | 28-29 | — | 80-90 | 220 | 2.0 |
| 16 | P3 | 97 | 28-29 | — | 80-90 | 220 | 2.0 |
| Comp. 19 | TRCl | 78 | 28-29 | 0.9 | 80-90 | 220 | 2.0 |

From a comparison between the comparative example and example 14, not only is the advantage of the increase in the polymerization yields by about 20% (as also shown even more distinctly in Table 2 for the tests in solution) evident, but also an improvement in the composition homogeneity in the polymeric chain (comparing the values of r$_E$xr$_p$ indicated in the table).

Furthermore, as for the tests in solution, the yields are higher when using the chlorinated activators of the present invention.

The invention claimed is:

1. A process for the (co)polymerization of olefins, comprising:
    polymerizing one or more of olefins in the presence of a catalytic system comprising:
    (a) a vanadium complex having the general formula L$_p$VO$_q$ wherein: i) p is an integer ranging from 2 to 4; ii) q can have the values of 0 or 1; iii) the sum p+q must be 3 or 4; and iv) L is a halogen or a beta-dicarbonyl group;
    (b) a chlorinated aluminum alkyl having the general formula Al$_y$R'''$_{3y-z}$Cl$_z$ wherein: R''' represents a linear or branched alkyl group, containing from 1 to 20 carbon atoms; "y"1 or 2; "z" is an integer ranging from 1 to 3y-1; and
    (c) a chlorinated promoter of formula (1)

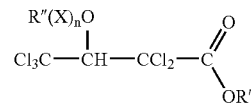

wherein: X represents a (—CO—) carbonyl or (—SO$_2$—) sulfonyl group;
n is 0 or 1;
R' is an alkyl or alkylaryl group having from 1 to 20 carbon atoms, optionally halogen substituted; and
R''=R', H.

2. The process according to claim 1, wherein L=Cl in the vanadium complex having the general formula L$_p$ VO$_q$.

3. The process according to claim 1, wherein, in the vanadium complex having the general formula L$_p$ VO$_q$, L is a beta-dicarbonyl group selected from acetyl-acetonate, formylacetonate, benzoylacetonate.

4. The process according to claim 1, wherein, in the compound Al$_{3y-z}$Cl$_z$, R''' is an alkyl group having from 1 to 4 carbon atoms.

5. The process according to claim 1, wherein the molar ratio between the chlorinated aluminum alkyl and the vanadium complex ranges from 1 to 1,000.

6. The process according to claim 5, wherein the molar ratio between the chlorinated aluminum alkyl and the vanadium complex ranges from 3 to 100.

7. The process according to claim 6, wherein the molar ratio between the chlorinated aluminum alkyl and the vanadium complex ranges from 5 to 50.

8. The process according to claim 1, wherein the molar ratio between the chlorinated promoter having general formula 1 and the vanadium ranges from 1 to 40.

9. The process according to claim 8, wherein the molar ratio between the chlorinated promoter having general formula 1 and the vanadium ranges from 1 to 10.

10. The process according to claim 1, wherein the polymerizing is carried out at a temperature in the range of from 10-30°C and the a pressure of from 5 to 20 atm.

11. The process according to claim 1, wherein the polymerizing is carried out in solution.

12. The process according to claim 1, wherein the polymerizing is carried out in suspension.

13. The process according to claim 1, wherein the chlorinated compound having general formula (1) is selected from the group consisting of ethyl 2,2,4,4,4-pentachloro-3-heptanoyloxybutyrate (formula 1: $R'=C_2H_5$, n=1; X=CO; $R''=CH_3(CH_2)_6$;

ethyl 2,2,4,4,4-pentachloro-3-hydroxybutyrate (formula 1: $R'=C_2H_5$, n=0; $R''=H$); ethyl 2,2,4,4,4-pentachloro-3-acetoxybutyrate (formula 1: $R'=C_2H_5$, n=1; X=CO; $R''=CH_3$; and ethyl 2,2,4,4,4-pentachloro-3-trifluoromethanesulfonyloxybutyrate (formula 1: $R'=C_2H_5$; n=1; $X=SO_2$, $R''=CF_3$).

14. The process of claim 1, wherein the polymerizing includes contacting a mixture of ethylene and propylene with the catalytic system to form an ethylene/propylene elastomeric copolymer.

15. The process of claim 1, wherein the polymerizing includes contacting a mixture comprising ethylene, propylene and at least one diene with the catalytic system to form an elastomeric copolymer.

* * * * *

UNITED STATES PATENT AND TRADEMARK OFFICE
CERTIFICATE OF CORRECTION

| | |
|---|---|
| PATENT NO. | : 7,514,386 B2 |
| APPLICATION NO. | : 11/137571 |
| DATED | : April 7, 2009 |
| INVENTOR(S) | : Bonsignore et al. |

It is certified that error appears in the above-identified patent and that said Letters Patent is hereby corrected as shown below:

On the title page, Item (75), the Inventors' information is incorrect. Item (75) should read:

-- (75) Inventors: Stefanio Bonsignore, Novara (IT); Marco Ricci, Novara (IT); Antonio Alfonso Proto, Novara (IT); Roberto Santi, deceased, late of Novara, (IT); by Maria Rivellini, legal representative, Novara (IT); by Laura Santi, legal representative, Novara (IT); by Stefano Santi, legal representative, Novara (IT); Gian Paolo Ravanetti, Ostiglia (IT); Andrea Vallieri, Bologna (IT)--

Signed and Sealed this

Twenty-eighth Day of July, 2009

JOHN DOLL
*Acting Director of the United States Patent and Trademark Office*